US011382504B2

(12) United States Patent
Robledo et al.

(10) Patent No.: US 11,382,504 B2
(45) Date of Patent: Jul. 12, 2022

(54) OCT SYSTEM AND OCT METHOD

(71) Applicant: HAAG-STREIT AG, Koeniz (CH)

(72) Inventors: Lucio Robledo, Bern (CH); Peter Stalder, Niederhünigen (CH); André Huber-Meznaric, Köniz (CH)

(73) Assignee: Haag-Streit AG, Koeniz (CH)

( * ) Notice: Subject to any disclaimer, the term of this patent is extended or adjusted under 35 U.S.C. 154(b) by 0 days.

(21) Appl. No.: 17/259,046

(22) PCT Filed: Jul. 2, 2019

(86) PCT No.: PCT/EP2019/067676
§ 371 (c)(1),
(2) Date: Jan. 8, 2021

(87) PCT Pub. No.: WO2020/011593
PCT Pub. Date: Jan. 16, 2020

(65) Prior Publication Data
US 2021/0244269 A1    Aug. 12, 2021

(30) Foreign Application Priority Data
Jul. 11, 2018    (EP) .................................. 18182845

(51) Int. Cl.
*G01B 9/02*    (2022.01)
*A61B 3/10*    (2006.01)
(Continued)

(52) U.S. Cl.
CPC .......... *A61B 3/102* (2013.01); *G01B 9/02028* (2013.01); *G01B 9/02091* (2013.01)

(58) Field of Classification Search
CPC ................ A61B 3/102; G01B 9/02028; G01B 9/02091; G01B 9/02004
See application file for complete search history.

(56) References Cited

U.S. PATENT DOCUMENTS

| 7,480,059 B2 | 1/2009 | Zhou et al. |
| 2012/0327423 A1* | 12/2012 | Hanebuchi ......... G01B 9/02028 356/497 |

(Continued)

FOREIGN PATENT DOCUMENTS

| CN | 102283635 A | 12/2011 |
| CN | 103251382 A | 8/2013 |

(Continued)

OTHER PUBLICATIONS

English Translation of PCT International Preliminary Report on Patentability for International application No. PCT/EP2019/067676 filed Jul. 2, 2019; Date of Completion: Oct. 13, 2020, dated Jan. 14, 2021; 6 pgs.

(Continued)

*Primary Examiner* — Tarifur R Chowdhury
*Assistant Examiner* — Jonathon Cook
(74) *Attorney, Agent, or Firm* — Alix, Yale & Ristas, LLP

(57) ABSTRACT

The invention relates to an OCT system, comprising: an OCT light source for emitting OCT light into an object beam path and a reference beam path; and a detector for capturing an interference signal produced from the object beam path and the reference beam path. A wavelength-dependent beamsplitter is arranged in the OCT beam path such that a first spectral partial beam is guided along a longer path and a second spectral partial beam is guided along a shorter path. The invention further relates to a corresponding OCT method. Two measurement regions separated from each other can be sensed by means of the OCT system according to the invention.

14 Claims, 6 Drawing Sheets

(51) Int. Cl.
*G01B 9/02015* (2022.01)
*G01B 9/02091* (2022.01)

(56) References Cited

U.S. PATENT DOCUMENTS

| | | | |
|---|---|---|---|
| 2014/0125951 A1* | 5/2014 | Eom | A61B 3/102 351/206 |
| 2015/0201833 A1* | 7/2015 | Chong | G01B 9/02004 351/206 |
| 2018/0206716 A1* | 7/2018 | Chong | A61B 3/14 |
| 2018/0242838 A1* | 8/2018 | Sarunic | G02B 21/0076 |

FOREIGN PATENT DOCUMENTS

| | | |
|---|---|---|
| CN | 103565405 A | 2/2014 |
| EP | 2564767 A1 | 3/2013 |
| EP | 2719324 A2 | 4/2014 |
| WO | 0138820 A1 | 5/2001 |
| WO | 2016196463 A1 | 12/2016 |

OTHER PUBLICATIONS

Shanhui Fan, et al. "Dual Band Dual Focus Optical Coherence Tomography For Imaging The Whole Eye Segment", Biomedicaloptics Express, vol. 6, No. 7 Jul. 1, 2015, XP0555-1126, DOI: 10.1364/BOE.6.002481, ISSN: 2156-7085, 14 pgs.
PCT International Research Report and Written Opinion for International File No. PCT/EP2019/067676 filed Jul. 2, 2019, dated Aug. 16, 2019, 6 pgs.
Bouma B. E. et al.: "Wide Tuning Range Wavelengh-Swept Laser with Two Semiconductor Optical Amplifiers", IEEE Photonics Technology Letters, IEEE Service Center, Piscata Way, NJ, US, vol. 17, No. 3, Mar. 1, 2005, pp. 678-680, XP01116989, ISSN: 1041-1135, DOI: 10.1109/LPT.2004.841003, 8 pgs.
Chinese Search Report for Application No. 2019800466500 filed Jul. 2, 2019; dated Jun. 29, 2021; 2 pgs.

\* cited by examiner

OCT SYSTEM AND OCT METHOD

BACKGROUND

The invention relates to an OCT system comprising an OCT light source for emitting OCT light into an object beam path and a reference beam path. An interference signal generated from the object beam path and the reference beam path is picked up by a detector. The invention additionally relates to an OCT method.

Optical coherence tomography (OCT) is an imaging measurement method. OCT light is guided onto an object, in particular human tissue. Scattering centers in the object are deduced from the reflected portions of the light. To that end, the object beam path reflected back from the object is superimposed with a reference beam path. The image information is obtained by evaluating the interference signal of the two beam paths.

The axial measurement depth is generally limited in OCT measurements. The interference signal has the highest signal strength if the optical path length in the reference beam path and the optical path length in the object beam path have the same length. A point in the object region for which this is the case is referred to as a reference point of the OCT measurement. By means of Fourier domain OCT (FD-OCT), it is also possible to identify scattering centers that are at a distance from the reference point. The greater the axial distance between an object point and the reference point, the weaker, however, the interference signal in this case and the poorer the quality of image information derived from the interference signal.

If an OCT device is used for ophthalmology measurements, then a front section of the eye and a back section of the eye are often of interest. The front section of the eye comprises the cornea and the eye lens. The back section of the eye comprises the retina. If a measurement extending over the front section of the eye and the back section of the eye is performed, then a significant portion of the image data relates to a region located between the front section of the eye and the back section of the eye. This portion of the image data has no relevant information content.

It is known provide two separate OCT interferometers, one interferometer being used for the front section of the eye and one interferometer being used for the back section of the eye, EP 2 719 324 A2. This solution is costly because the essential components of the OCT system have to be present twice. This also applies to solutions which employ separate light sources and separate detector units for each of the measurement regions, WO 2001/038820 A1. Also known is an OCT system which switches mechanically between a path for the front section of the eye and a path for the back section of the eye, U.S. Pat. No. 7,480,059 B2. Mechanical switchovers have the disadvantage that the switchover requires time, during which the measurement object may move. This movement results in inaccuracies in the spatial assignment of the measurement data. No measurement data can be acquired during the switchover, and so the measurement duration is lengthened by the switchover duration. Furthermore, with a mechanical measurement region switchover it is necessary to synchronize the point in time of the switchover with the detection of the interferometric measurement.

SUMMARY OF THE INVENTION

The invention is based on the object of presenting an OCT system and an OCT method such that two separate measurement regions can be detected with little outlay. Proceeding from the prior art cited, the object is achieved by means of the features of the independent claims. Advantageous embodiments are specified in the dependent claims.

In the OCT system according to the invention, a wavelength-dependent beam splitter is arranged in the OCT beam path, such that a first spectral partial beam is guided along a longer path distance and that a second spectral partial beam is guided along a shorter path distance.

The OCT system comprises a unified OCT light source which provides the OCT light for the first spectral partial beam and the second spectral partial beam. The OCT system comprises a unified detector which picks up the interference signal generated from the first spectral partial beam and the interference signal generated from the second spectral partial beam.

Splitting the OCT light by means of a wavelength-dependent beam splitter makes it possible to guide different frequency ranges of the OCT light without mechanical switchover along two different path distances. Two measurement regions separated from one another can thus be detected in one unified measurement process.

The OCT system can comprise a separating beam splitter, which splits the OCT light emitted by the OCT light source into the object beam path and the reference beam path. The separating beam splitter is preferably not wavelength-dependent, such that the splitting into the object beam path and the reference beam path encompasses the entire spectrum emitted by the OCT light source.

The OCT system can comprise an interference beam splitter, in which the OCT light from the object beam path and the OCT light from the reference beam path are caused to interfere. The separating beam splitter and the interference beam splitter can be two mutually separate optical components. In one embodiment, the separating beam splitter and the interference beam splitter are realized in one optical component. In this case, the splitting into the object beam path and the reference beam path can be effected when the OCT light impinges on the optical component in one direction. The interference signal can be generated when the OCT light impinges on the optical component in another direction, in particular in the opposite direction.

The object beam path can extend from the separating beam splitter via the measurement object to the interference beam splitter. The reference beam path can extend from the separating beam splitter via a reference mirror as far as the interference beam splitter. It is also possible for the reference beam path to extend along an optical waveguide from the separating beam splitter to the interference beam splitter.

The OCT beam path can comprise a parallel section, in which the first spectral partial beam is guided along a first parallel path and in which the second spectral partial beam is guided along a second parallel path. The first parallel path can be longer than the second parallel path. After emerging from the parallel section, the first spectral partial beam and the second spectral partial beam can be recombined, wherein the two spectral partial beams can be coaxial or non-coaxial after emerging from the parallel section. The parallel section can form a section of the object beam path or can form a section of the reference beam path. The term OCT beam path is used as a generic term for the object beam path and the reference beam path.

A first wavelength-dependent beam splitter can be arranged at the input of the parallel section. A first spectral portion of the OCT light can be guided onto the first parallel path by the first wavelength-dependent beam splitter, while a second spectral portion of the OCT light is guided onto the second parallel path.

A second wavelength-dependent beam splitter can be arranged at the output of the parallel section. Upon emerging from the parallel section, the two spectral partial beams can be recombined by the second wavelength-dependent beam splitter to form a common OCT beam path. The optical properties of the two wavelength-dependent beam splitters can be identical.

The OCT beam path can be configured such that light passes through the parallel section twice. The order in which the OCT light impinges on the wavelength-dependent beam splitters can be reversed in the case of the second pass by comparison with the first pass. In the case of the second pass, the OCT beam path can be split at the second wavelength-dependent beam splitter and the two partial beams can be combined at the first wavelength-dependent beam splitter.

In order that the path distance for the two spectral partial beams is configured with different lengths within the parallel section, a partial beam mirror can be arranged within the parallel section. The term partial beam mirror denotes a mirror which is arranged in the beam path of one of the spectral partial beams, but not in the beam path of the other spectral partial beam. The term mirror denotes generally an optical element that deflects the direction of a beam path.

The parallel section can comprise two partial beam mirrors, which deflect the first spectral partial beam by 180° between the wavelength-dependent beam splitters. The second spectral partial beam can take a straight path between the two wavelength-dependent beam splitters.

The path length difference between the first parallel path and the second parallel path can be adjustable. This can be realized by altering the distance between a partial beam mirror of the parallel section and a wavelength-dependent beam splitter. The partial beam mirror can be arranged in a fixed position and the wavelength-dependent beam splitter can be moved. Alternatively, the wavelength-dependent beam splitter can be arranged in a fixed position and the partial beam mirror can be displaceable. In both cases, either the longer path distance of the first spectral partial beam or the shorter distance of the second spectral partial beam can be adjustable in length. It is also possible that the two elements can be displaced independently of one another. The adjustment of the distance can be driven manually or by motor.

In one embodiment, the parallel section comprises a first partial beam mirror and a second partial beam mirror. For adjusting the path length difference, the distance between the first partial beam mirror and the first wavelength-dependent beam splitter and the distance between the second partial beam mirror and the second wavelength-dependent beam splitter can be altered simultaneously. Simultaneously adjustable means that the two distances are changed by the same magnitude in each case. The distances can be identical.

The measurement object on which the OCT system is used can be an eye, in particular a human eye. The range of adjustment of the optical elements in the parallel section of the OCT beam path can be dimensioned such that, in a first configuration of the parallel section, the first object region examined by the first spectral partial beam and the second object region examined by the second spectral partial beam are both arranged in a front section of the eye. The first object region can comprise the cornea of the eye. The second object region can comprise the eye lens of the eye. In a second configuration of the parallel section, the first object region can be arranged in a front section of the eye and the second object region can be arranged in a back section of the eye.

The OCT system can be configured such that in a first state a wavelength-dependent beam splitter is arranged in the OCT beam path and that in a second state the wavelength-dependent beam splitter is not arranged in the OCT beam path. This preferably applies to all wavelength-dependent beam splitters arranged in the OCT beam path in the first state. Without a wavelength-dependent beam splitter in the OCT beam path, the parallel section is omitted and the entire spectrum of the OCT light covers the same path distance. A single object region can then be examined by the OCT system, the axial resolution being increased in comparison with the parallel examination of two object regions.

The OCT system can comprise a switching module comprising the wavelength-dependent beam splitters, which switching module is used to switch between the first state and the second state of the OCT system. The switching movement during the change between the states can be a lateral movement relative to the optical axis. In this case, the switching module can carry out a pivoting movement and/or a translational movement. The movement can be driven manually or by motor. The switching module can additionally be displaceable along the optical axis in order to adjust the path length difference between the two spectral partial beams.

In one embodiment, switching movement during the change between the first state and the second state is a movement parallel to the optical axis, wherein the switching module is designed such that the movement parallel to the optical axis is converted into a lateral movement of the wavelength-dependent beam splitters. This has the advantage that a single actuator can be sufficient both for adjusting the path length difference and for changing between the first state and the second state. By way of example, the switching module displaced parallel to the optical axis in order to adjust the path length difference can strike a stop at the end of the range of adjustment, such that upon further displacement of the switching module a movement is triggered within the switching module, by way of which movement the wavelength-dependent beam splitters are removed from the OCT beam path. The movement can be a pivoting movement of a beam splitter unit comprising the two wavelength-dependent beam splitters. It is desirable for the beam splitter unit to have an exactly defined position when the wavelength-dependent beam splitters are arranged in OCT beam path. By way of example, the beam splitter unit can be held in its position within the switching module by a spring and/or by a magnet.

The OCT beam path can be in a collimated state upon impinging on the first wavelength-dependent beam splitter. A collimation optical unit that brings the OCT beam path into this state can be arranged between the separating beam splitter and the first wavelength-dependent beam splitter. The parallel section of the OCT beam path can be configured such that the beam path is deflected, but not altered in its shape. The two spectral partial beams can still be in a collimated state upon leaving the parallel section. If the parallel section is arranged in the object beam path, an objective lens that focuses the two spectral partial beams in the object region can be arranged between the parallel section and the measurement object. The focus of the two spectral partial beams can lie in the same object plane.

If the two spectral partial beams are used to obtain image information from two object regions spaced apart from one another in an axial direction, it can be advantageous if the axial focus position of the first spectral partial beam deviates from the axial focus position of the second spectral partial beam. The term axial focus position denotes the focus position along the optical axis of the objective lens. The OCT system can comprise a partial beam lens arranged in the beam path of one of the two spectral partial beams, but not in the beam path of the other of the two spectral partial beams. The term lens denotes generally a light-refracting optical component. The partial beam lens can be adjustable, such that the focus position of the relevant spectral partial beam can be displaced in an axial direction. By way of example, the partial beam lens can be displaceable along the optical axis. A lens arranged in a fixed position and having a variable refractive power, for example in the form of a liquid lens, is also possible.

The partial beam lens can be arranged such that together with the objective lens it shapes a beam path that does not have a focus lying in the object region. By way of example, the beam path can be collimated. A slightly divergent shape or a slightly convergent shape is also possible, in the latter case the focus lying at least 20 cm behind the object region. In particular, the partial beam lens can be arranged such that it focuses the spectral partial beam in a device-side focal plane of the objective lens. An opposite configuration is also possible, in which the objective lens alone does not focus the beam path in the object region and in which the partial beam lens together with the objective lens forms a partial beam focused in the object region.

Such an OCT system is suitable in particular for measurements on the eye. Image information of the front section of the eye can be obtained by means of the partial beam focused in the object region. The non-focused or collimated beam path can enter the eye and be focused in the back section of the eye by the cornea and the eye lens. Thus, both the front section of the eye and the back section of the eye can be examined by means of one focused OCT beam.

The OCT system can comprise a scanning device in order to deflect the object beam path in a lateral direction. Sectional images of the measurement object can be generated by deflection in a lateral direction. If the scanning device is designed to deflect the object beam path in two lateral directions (for example X-direction, Y-direction), a three-dimensional volume image can be constituted from a plurality of sectional images. The scanning device can be arranged in the total beam of the object beam path, that is to say outside the parallel section.

The scanning device can comprise two scanning mirrors, for example, which are pivotable about mutually orthogonal axes. Such an arrangement of scanning mirrors is a conventional example of a scanning device that can be used to scan a measurement object. The scanning device can alternatively also comprise a single mirror, which is tiltable along two non-parallel axes. The non-parallel axes can be orthogonal to one another or non-orthogonal to one another. The scanning device can be arranged between a collimation optical unit and an objective lens of the object beam path. The optical unit of the object beam path can be designed in a telecentric fashion, such that the scanning device is arranged at a focal point of the objective lens and the beam path between the objective and the measurement object is displaced in a parallel fashion during scanning. The parallel displacement can relate to the first spectral partial beam and the second spectral partial beam.

In the case where the OCT system is used on the human eye, the first spectral partial beam, which covers the longer distance in the parallel section, is normally used for scanning the front section of the eye. The second spectral partial beam, which covers the shorter distance in the parallel section, is used for scanning the back section of the eye. If the second spectral partial beam is offset in a parallel fashion jointly with the first spectral partial beam, then the second spectral partial beam is always guided onto the same region of the retina by the cornea and the eye lens despite the parallel displacement.

In order to enable imaging of the back section of the eye as well, the OCT system can be configured such that the second spectral partial beam impinges on the measurement object at a different angle than the first spectral partial beam. In particular, the first spectral partial beam can be guided onto the measurement object parallel to the optical axis of the objective. This can apply to any position of the scanning device. The second spectral partial beam can impinge on the measurement object at a different angle. The angle can change depending on the position of the scanning device. There may be a position of the scanning device in which the second spectral partial beam also impinges on the measurement object parallel to the optical axis of the objective.

For this purpose, the OCT system can comprise a total beam lens arranged outside the parallel section, which total beam lens focuses the two spectral partial beams within the parallel section. This results in a first focal point in the parallel path of the first spectral partial beam and a second focal point in the parallel path of the second spectral partial beam. The total beam lens can be arranged between the separating beam splitter and the parallel section. The total beam lens can be arranged such that the OCT beam path impinges on the total beam lens in the collimated state.

In one embodiment, the total beam lens is arranged between the scanning device and the parallel section. Moreover, the total beam lens can be arranged between the separating beam splitter and the parallel section. As a result of the scanning device being actuated, the first focal point and the second focal point are displaced laterally in each case. A partial beam lens can be arranged in the parallel path of the first spectral partial beam, which partial beam lens puts the first spectral partial beam into a collimated state again. The first spectral partial beam can be guided onto the objective lens in the collimated state, such that the first spectral partial beam is focused in the object region by the objective lens.

The second spectral partial beam can impinge on the objective lens in a divergent state. If the distance between the second focal point and the objective lens corresponds to the focal length of the objective lens, the second spectral partial beam is put into a collimated state by the objective lens. The lateral offset of the second focal point is converted into a change in direction by the objective lens. By virtue of the second focal point being displaced laterally by the scanning device, the direction from which the second spectral partial beam impinges on the measurement object thus changes. If the measurement object is an eye, the different directions are translated into different positions in the back section of the eye.

The wavelength-dependent beam splitter can have a limit wavelength, such that wavelengths above the limit wavelength are guided into one spectral partial beam and wavelengths below the limit wavelength are guided into the other spectral partial beam. The limit wavelength can lie approximately centrally within the frequency band of the OCT light. This results in an approximately equally good axial resolution of the object regions examined by means of both spectral partial beams. A limit wavelength arranged eccentrically within the frequency band is also possible, such that the resolution in one object region is increased at the expense of the resolution in the other object region. It is also possible to use a beam splitter with an adjustable limit wavelength, thus making it possible to vary the resolution capability between the two object regions.

The OCT beam path can impinge on the wavelength-dependent beam splitter as a free beam. The wavelength-dependent beam splitter can be embodied as a dichroic splitter mirror, which reflects one portion of the frequencies of the OCT light and transmits another portion of the frequencies of the OCT light. Such beam splitters are glass substrates having a dielectric coating which either reflect or transmit OCT light depending on the frequency. Dichroic splitter mirrors are usually designed for an angle of incidence of 45°. Dichroic splitter mirrors having exactly one transmission band and exactly one reflection band within the spectrum of the OCT light are particularly suitable. The transmission band is the wavelength interval in which the beam splitter predominantly transmits; correspondingly, the reflection band is the wavelength interval in which the beam splitter predominantly reflects. The limit wavelength of the dichroic beam splitter corresponds to that wavelength between transmission band and reflection band for which the light power transmitted is approximately the same as that reflected. The transmission band can comprise wavelengths that are longer than the limit wavelength; the reflection band then comprises wavelengths that are shorter than the limit wavelength ("long-pass"). An opposite configuration ("short-pass") is also possible. Dichroic beam splitters which have a high edge steepness, that is to say which transition from high transmission to high reflection in a very small wavelength interval, are particularly well suited. The beam splitter can transition from 20% transmission to 80% transmission within at most 2% of the cut-off wavelength, for example. In one advantageous embodiment, the beam splitter transitions from 10% transmission to 90% transmission within at most 0.7% of the cut-off wavelength.

It is furthermore advantageous if the dichroic splitter mirror has the lowest possible reflection in the transmission band and the lowest possible transmission in the reflection band. If the spectral separation contrast of the beam paths is too low, the signals of the two OCT measurement regions are separated only inadequately. Good dichroic splitter mirrors achieve a transmission of <1% in the reflection band and a reflection of <5% in the transmission band.

As an alternative to the free-beam arrangement, the OCT beam path and/or the spectral partial beams can also be guided within optical waveguides. The parallel section can comprise two mutually parallel optical waveguides of different lengths, between which the OCT light is split by wavelength-selective changeover switches. A wavelength-selective changeover switch is an alternative embodiment of a wavelength-dependent beam splitter. Such a fiber-based OCT system can comprise a bypass optical waveguide that bypasses the parallel section. Fiber-optic switching elements can be used to switch the OCT beam path between the parallel section and the bypass optical waveguide. If the OCT beam path passes through the parallel section, two object region can be examined with reduced resolution. If the OCT beam path passes through the bypass optical waveguide, then one object region can be examined with increased resolution.

The light source of the OCT system can be a swept-source light source, in which narrowband OCT light is tuned over a spectral tuning range within a tuning time (swept-source OCT, SS-OCT). The swept-source light source generates the first spectral partial beam and the second spectral partial beam by way of a unified tuning process. The interference signal generated by means of the first spectral partial beam is then temporarily separated from the interference signal generated by means of the second spectral partial beam. The two interference signals, picked up in a time-resolved manner by photodiodes, can be spectrally resolved separately from one another. The photocurrent of the photodiodes can be converted into a voltage and digitized. After the spectral resolution, the transformation into a spatial signal can be effected separately for both interference signals. In combination with the lateral deflection of the object beam path by the scanning device, sectional images of the measurement object can be created for each of the spectrally separate object regions measured.

The data acquisition of an SS-OCT interferometer can be configured such that the interference signal is detected in equidistant wavelength intervals $\delta k$ (see US 2008/0175465, for example). For a tunable light source having a tuning range $\Delta k$, a wavenumber $k_i = k_0 + i \cdot \delta k$ can be allocated to each detected measurement value within the tuning process, wherein i can assume values between 0 and $n = \Delta k / \delta k - 1$. Conversely, the interference signal can be described as a signal vector with a position index i. In order then to separate the interference signal into the two spectral channels (corresponding to the partial beams), the wavenumber of the limit wavelength of the dichroic mirror $k_d$ or the position in the signal vector, $j_d = (k_d - k_0) / \delta k$, is determined. The spectrally resolved signal for partial beam 1 is the signal vector with $i = 0 \ldots j_d - 1$; for partial beam 2, it corresponding holds true that $I = j_d \ldots n$. The two spectrally resolved signals can then be processed further independently of one another using known methods. The processing steps usually comprise at least multiplication by a window function, multiplication by a complex-valued vector and subsequent Fourier transformation. Depending on the properties of the dichroic beam splitter, it may also be expedient to process only a portion of the spectrally resolved signals. In particular, interference signals in the transition region of the dichroic beam splitter can be discarded in order to avoid insufficient channel separation.

Alternatively, the light source of the OCT system can be a broadband light source. A spectrometer is then used as a detector (spectral-domain OCT, SD-OCT). In order to separate the interference signal generated by means of first spectral partial beam from the interference signal generated by means of the second spectral partial beam, the interference signal detected by the spectrometer, minus the reference arm spectrum, is firstly transformed into a representation linearized in terms of wavenumber according to known methods. A procedure corresponding to that in the case of swept-source OCT can be adopted for the subsequent evaluation. The term Fourier domain OCT is used as a generic term for SS-OCT and SD-OCT.

The invention additionally relates to an OCT method in which OCT light is emitted and is split into an object beam path and a reference beam path. An interference signal generated from the object beam path and the reference beam path is picked up by a detector. A wavelength-dependent beam splitter is arranged in the OCT beam path, such that a first spectral partial beam is guided along a longer path distance and that a second spectral partial beam is guided along a shorter path distance.

The method can be developed with further features described in the context of the system according to the invention. The system can be developed with further features described in the context of the method according to the invention.

BRIEF DESCRIPTION OF THE DRAWINGS

The invention is described by way of example below on the basis of advantageous embodiments with reference to the accompanying drawings, in which.

DETAILED DESCRIPTION

Figure 1:
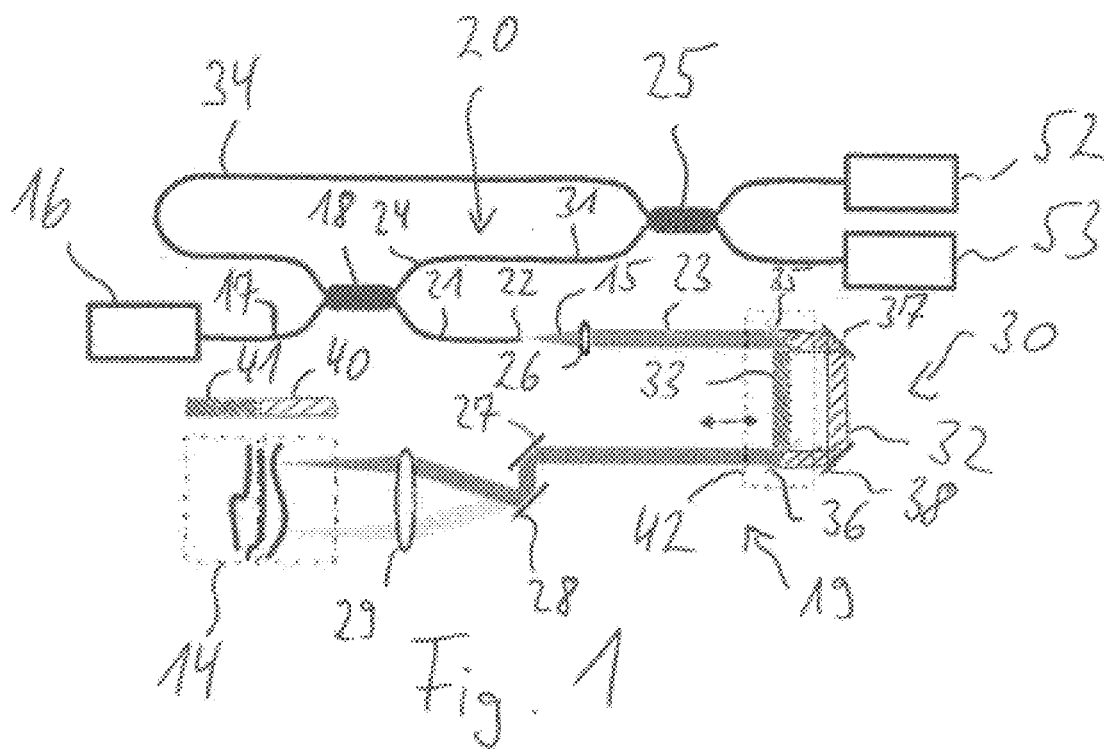
FIG. 1: shows a first embodiment of an OCT system according to the invention.

An OCT system shown in FIG. 1 serves for examining a measurement object 14, for example in the form of a human eye. By virtue of OCT light 15 being directed onto the measurement object 14, image information is obtained, which extends along the axis of the OCT beam into the depth of the measurement object 14. By virtue of the OCT beam being scanned over the measurement object 14 in a direction perpendicular thereto, a three-dimensional image of the measurement object 14 can be obtained from a multiplicity of individual measurement recordings.

The OCT system comprises an OCT light source 16, embodied as a swept-source light source. The swept-source light source 16 generates narrowband light that is spectrally tunable. That is to say at each instant narrowband light is emitted, the frequency of which changes over time, such that the swept-source light source is tuned over a frequency range during a tuning time.

The OCT light 15 emitted by the OCT light source 16 is fed into a first optical waveguide 17, embodied as a monomode optical waveguide. The first optical waveguide 17 extends to a separating beam splitter 18 in the form of a fiber coupler, in which the OCT light 15 from the first optical waveguide 17 is split into an object beam path 23 and a reference beam path 24. The object beam path 23 extends from the separating beam splitter 18 along an object arm 19 as far as the measurement object 14. The reference beam path 24 extends from the separating beam splitter 18 along a reference arm 20 as far as an interference beam splitter 25.

The object arm 19 comprises a second optical waveguide 21, which extends from the fiber coupler 18 as far as an exit end 22. At the exit end 22, the object beam path 23 emerges from the second optical waveguide 21 in a divergent state and is brought to a collimated state by a collimation lens 26.

A scanning device comprises two scanning mirrors 27, 28, which are pivotable about two mutually orthogonal axes. The object beam path 23 is guided to an objective lens 29 via the scanning device 27, 28. The object beam path 23 passes through the objective lens 29 and is focused in the region of the measurement object 14. The distance between the objective lens 29 and the second scanning mirror 28 corresponds to the focal length of the objective lens 29, such that the measurement object 40 is scanned independently of the distance with respect to the objective lens 29 by means of laterally offset measurement beams. Such an arrangement of objective lens 29 and scanning device 27, 28 is referred to as telecentric.

The direction from which the object beam path 23 impinges on the objective lens 29 changes by means of pivoting of the scanning mirrors 27, 28. Since the second scanning mirror 28 is arranged at the focal point of the objective lens 29, the beam path 23 extends between the objective lens 29 and the measurement object 14 parallel to the optical axis of the objective lens 29 independently of the position of the scanning device 27, 28.

Arranged between the collimation lens 26 and the scanning device 27, 28 is a parallel section 30 of the object beam path 23, in which a first spectral partial beam 32 and a second spectral partial beam 33 of the object beam path are guided along paths of different lengths. Before entering the parallel section 30 and after exiting the parallel section 30, the paths of the two spectral partial beams 32, 33 are identical.

OCT light reflected back from the measurement object 14 moves with an opposite direction of propagation along the object arm 19 back to the separating beam splitter 18 and through the separating beam splitter 18 along a third optical waveguide 34 as far as the interference beam splitter 25.

The reference arm 20 comprises a fourth optical waveguide 31, which extends from the separating beam splitter 18 as far as the interference beam splitter 25. The fourth optical waveguide 31, illustrated in a shortened manner in FIG. 1, is dimensioned such that the optical path length between the separating beam splitter 18 and the interference beam splitter 25 is of the same length in the object arm 19 and in the reference arm 20. The object beam path 23 and the reference beam path 24 are recombined in the interference beam splitter 25, with the result that an interference signal arises. The interference signal is all the stronger, the more OCT light is reflected back from a specific structure within the measurement object 14. Scattering centers within the measurement object 14 can thus be identified by the evaluation of the interference signal.

If a scattering center is arranged precisely at the reference point of the object beam path, then the optical path length of the object beam path 23 and that of the reference beam path 24 are exactly equal, thus resulting in a standing interference signal. If the scattering center is at a distance from the reference point, then the interference signal oscillates (in a spectral representation), the frequency becoming all the greater, the greater the distance with respect to the reference point.

The interference signals from the interference beam splitter 25, which interference signals are phase-shifted by 180°, are picked up by two detector elements 52, 53, which are parts of a unified detector within the meaning of the invention. By means of difference formation between the two detector elements 52, 53, the stationary portion of the signal can be eliminated, thus resulting in a useful signal with high resolution. The difference between the photocurrents of the detector elements 52, 53 is converted into a voltage and digitized. Sectional images of the measurement object 14 can be created by means of lateral deflection of the OCT beam by the scanning device 27, 28.

In the parallel section 30 of the object arm 19, the object beam path 23 impinges on a wavelength-dependent splitter mirror 35 in the form of a dichroic splitter mirror at an angle of 45°. Spectral splitting of the OCT light 15 is effected in the dichroic splitter mirror 35. Light portions whose frequency is greater than a limit wavelength of the dichroic splitter mirror 35 are reflected. Light portions whose frequency is less than a limit wavelength of the dichroic splitter mirror 35 are transmitted. The transmitted portion of the OCT light 15 forms the first spectral partial beam 32. The reflected portion of the OCT light 15 forms the second spectral partial beam 33.

The OCT light 15 emitted by the OCT light source 16 can extend for example over a wavelength spectrum of $\lambda$=1000 nm to $\lambda$=1100 nm. The first dichroic splitter mirror 35 can be embodied such that it has a high reflectivity for OCT light having a wavelength of less than $\lambda$=1045 nm and a high transmission for OCT light having a wavelength of more than $\lambda$=1055 nm.

The second spectral partial beam 33 impinges on a second wavelength-dependent splitter mirror 36, likewise embodied as a dichroic beam splitter. The second dichroic splitter mirror 36 has the same optical properties as the first dichroic splitter mirror 35. The second spectral partial beam 33 is thus also reflected at the second dichroic splitter mirror 36 and deflected in the direction of the scanning device 27, 28.

The first spectral partial beam 32 is guided via two mirrors 37, 38 to the second dichroic splitter mirror 36, such that within the parallel section 30, the first spectral partial beam 32 covers a longer distance than the second spectral partial beam 33. The mirrors 37, 38, which deflect only the first spectral partial beam 32, but not the second spectral partial beam 33, are partial beam mirrors 37, 38 within the meaning of the invention. The two spectral partial beams 32, 33 are recombined in the second dichroic splitter mirror 36. On the return path from the measurement object 14 to the interference beam splitter 25, the second spectral partial beam 33 again takes the direct path between the two dichroic splitter mirrors 35, 36, while the first spectral partial beam 32 again takes the longer path via the partial beam mirrors 37, 38. The path length difference between the two spectral partial beams 32, 33 thus doubles with passage twice through the parallel section 30.

The path length difference between the first spectral partial beam 32 and the second spectral partial beam 33 has the effect that the interference signal relates to structures of measurement object 14 which are spaced apart from one another axially. The first spectral partial beam 32, which covers a longer distance in the parallel section 30, generates an interference signal from a first object region 40, which is at a smaller distance from the objective lens 29. The second spectral partial beam 33, which covers a shorter distance in the parallel section 30, generates an interference signal from a second object region 41, which is at a larger distance from the objective lens 29. Since the swept-source light source 16 emits the different frequencies in a manner distributed over time, the interference signals from the object regions 40, 41 are temporally separated from one another. The image information can be evaluated separately according to the temporal separation. To that end, the interference signal is firstly digitized in a spectrally resolved manner and then transformed into a spatial signal. In the case of SD-OCT, in which all frequencies simultaneously impinge on the object, the interference signal detected by the spectrometer, minus the reference arm spectrum, is transformed into a representation linearized in terms of wavenumber according to known methods before the evaluation separated according to the object regions is effected.

A switching module 42 comprising the two dichroic splitter mirrors 35, 36 is mounted displaceably, such that the distance between the two dichroic splitter mirrors 35, 36 and the two partial beam mirrors 37, 38 is adjustable. The switching module 42 can be displaced manually or by motor.

Figure 2:
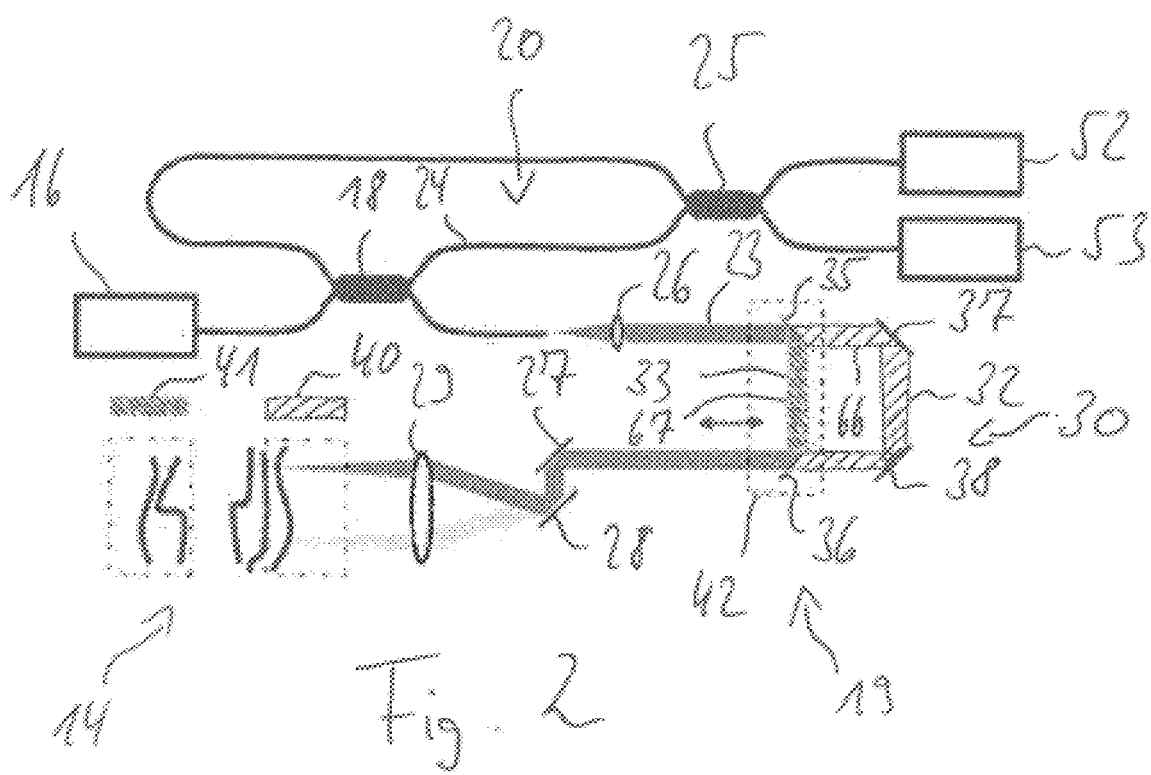
FIG. 2: shows the OCT system from FIG. 1 in another state.

FIG. 2 shows a state of the OCT system in which the two dichroic splitter mirrors 35, 36 are at a greater distance from the two partial beam mirrors 37, 38 than in FIG. 1. The position of the first object region 40 scanned by means of the first spectral partial beam 32 remains unchanged. The position of the second object region scanned by means of the second spectral partial beam 33 is displaced toward the rear, such that the distance between the two object regions 40, 41 is increased. Both in FIG. 1 and in FIG. 2, the distance between the two object regions 40, 41 corresponds to the distance between the first dichroic splitter mirror 35 and the first partial beam mirror 37 plus the distance between the second dichroic splitter mirror 36 and the second partial beam mirror 38.

Figure 10:
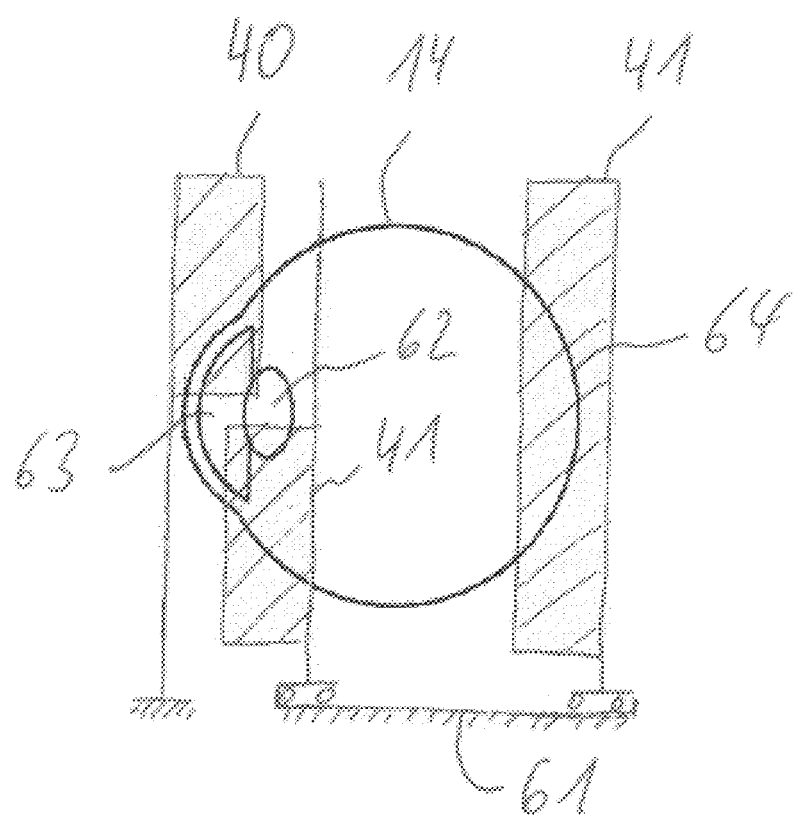
FIG. 10: shows one example of a measurement object of an OCT system according to the invention.

FIG. 10 illustrates a human eye, which can serve as a measurement object 14 of the OCT system. The first object region 40 of the OCT system is positioned such that it covers the cornea 63 of the eye. The two variants in accordance with FIGS. 1 and 2 are illustrated for the second object region 41. If the two object regions 40, 41 are directly adjacent to one another in accordance with FIG. 1, then the second object region 41 covers the eye lens 62. If the two object regions 40, 41 are spaced apart from one another, as shown in FIG. 2, then the retina 64 of the eye can be examined by way of the second object region 41. The displacement mechanism 61 that can be used to displace the switching module 42 between the positions is indicated schematically in FIG. 10. If the displacement mechanism 61 is actuated beyond a stop, the splitter mirror unit 42 is removed from the object beam path 23 by means of a pivoting movement.

Figure 3:
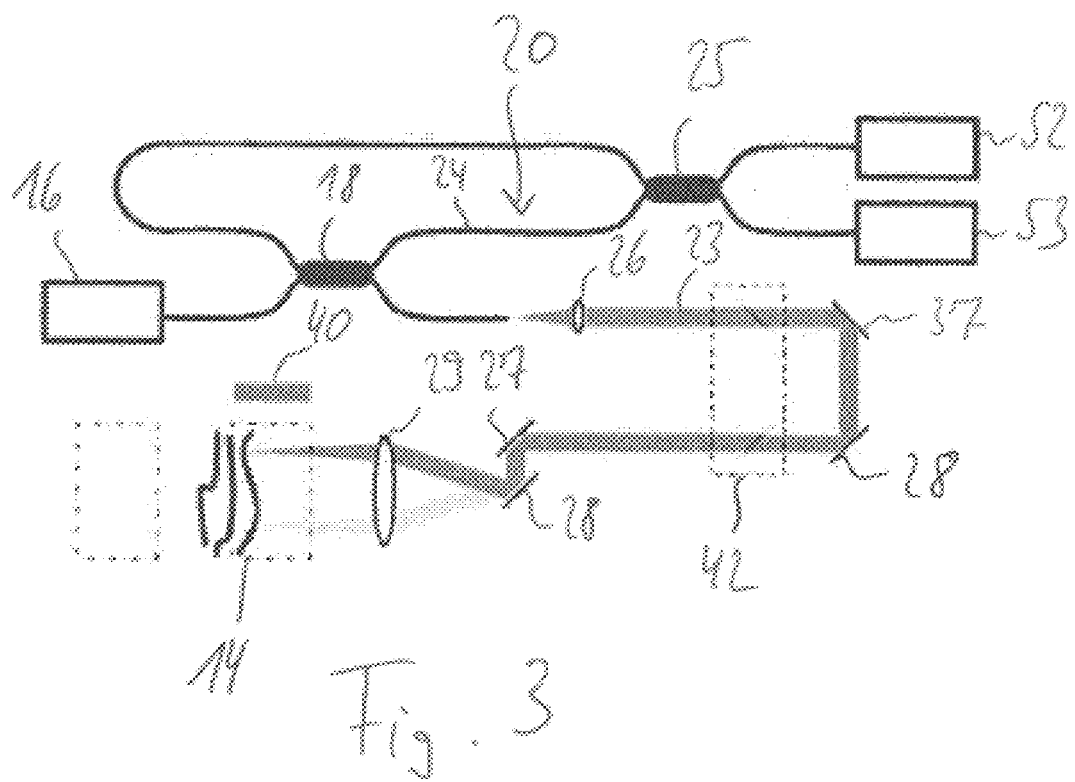
FIG. 3: shows the OCT system from FIG. 1 in yet another state.

FIG. 3 illustrates the OCT system in a state in which the splitter mirror unit 42 has been removed from the object beam path 23. The OCT light in its entirety takes the path of the first spectral partial beam 32, which otherwise is taken only by the light transmitted by the dichroic splitter mirrors 35, 36. An interference signal arises only as a result of the light backscattered from the first object region 40. On account of the higher bandwidth of the OCT light, the image resolution is improved compared with image information that is derived only from the first spectral partial beam 32. A pivoting mechanism can be provided which enables the switching module 42 to be pivoted into the object beam path 23 and out of the latter. The pivoting movement of the switching module 42 can be driven manually or by motor.

Figure 4:
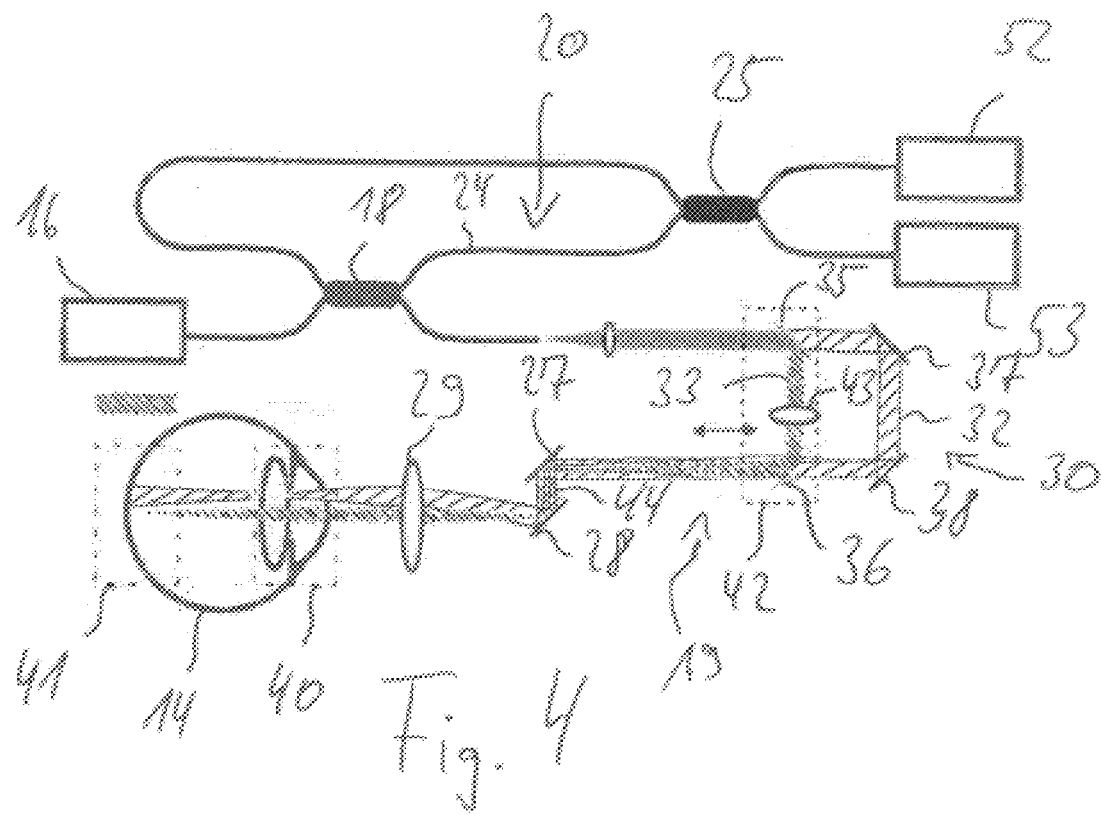
FIG. 4: shows an alternative embodiment of an OCT system according to the invention.

In the case of the OCT system illustrated in FIG. 4, the first object region 40 corresponds to the front section and the second object region 41 to the back section of a human eye. The OCT system is positioned in front of the eye such that the first spectral partial beam 32 is focused onto the front section 40 of the eye.

In the second spectral partial beam 33, a partial beam lens 43 is arranged between the two dichroic splitter mirrors 35, 36 and focuses the second spectral partial beam 33 onto a focal point 44, which is arranged between the two scanning mirrors 27, 28 in this example. The distance between the focal point 44 and the objective lens 29 corresponds to the focal length of the objective lens 29, such that the second spectral partial beam 32 is brought to a collimated state upon passing through the objective lens 29. By virtue of the refractive power of the cornea and the eye lens of the eye 14, the second spectral partial beam 33 is focused onto the back section 41 of the eye. This OCT system thus enables sharply resolved measurement values to be obtained both from the front section 40 of the eye and from the back section 41 of the eye. The partial beam lens 43 can be configured as a lens having a variable refractive power, for example in the form of a liquid lens. This makes it possible to position the focus of the beam path on the front section 40 of the eye or the back section 41 of the eye, depending on the measurement region position.

Figure 5:
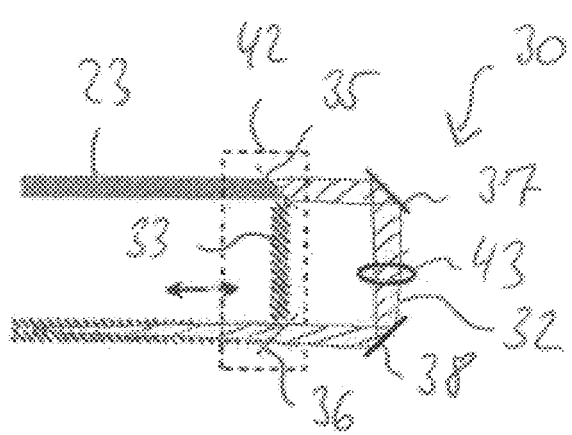
FIG. 5: shows a detail of an OCT system according to the invention.

FIG. 5 illustrates a variant in which the partial beam lens 43 is arranged in the first spectral partial beam 32, rather than in the second spectral partial beam 33. This position of the partial beam lens 43 may be advantageous depending on the properties and the arrangement of the other lenses in the object beam path 23.

Figure 6:
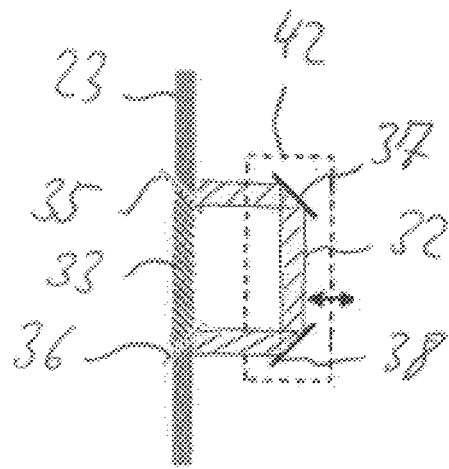
FIG. 6: shows the view in accordance with FIG. 5 in the case of an alternative embodiment.

In the case of the further variant in accordance with FIG. 6, the conditions in the case of the dichroic splitter mirrors 35, 36 are reversed. The first spectral partial beam 32 is reflected at the dichroic splitter mirrors 35, 36, while the second spectral partial beam 33 is transmitted by the dichroic splitter mirrors 35, 36. By displacing the unit 42 comprising the partial beam mirrors 37, 38, it is possible to alter the path length of the first spectral partial beam 32. The position of the second object region 41 thus remains unchanged, while the position of the first object region 40 is displaced. If the two dichroic splitter mirrors 35, 36 are removed from the beam path in this variant, then a measurement in the back object region 41 with increased axial resolution is possible.

Figure 7:
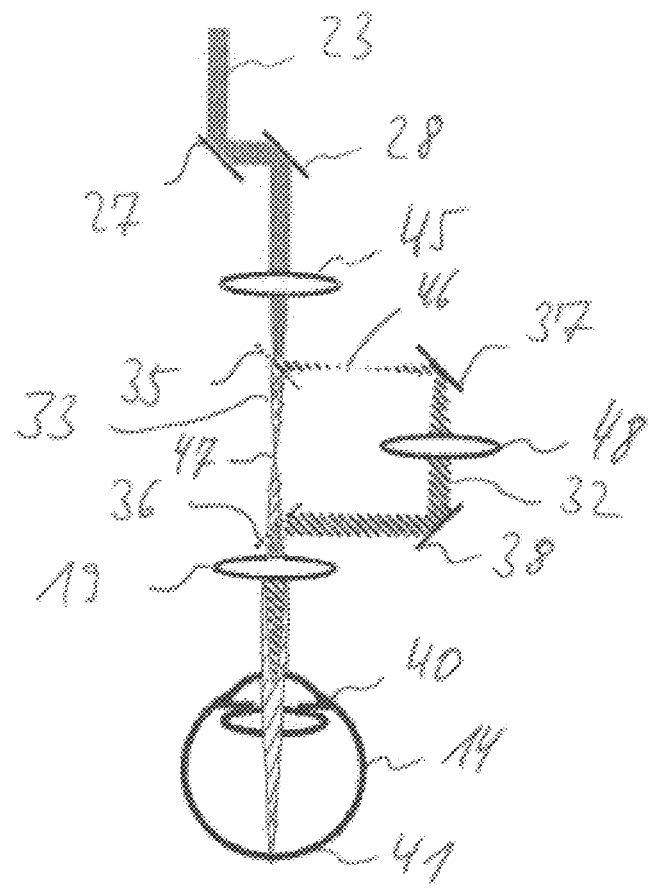
FIGS. 7-9: show details of OCT systems according to the invention in the case of alternative embodiments of the invention.

FIG. 7 shows a variant with a somewhat different configuration of the object arm 19. The scanning device 27, 28 is arranged upstream of the first dichroic splitter mirror 35, and a lens 45 is situated between the scanning device 27, 28 and the first dichroic splitter mirror 35, the entire object beam path 23 passing through said lens. The lens 45 is a total beam lens within the meaning of the invention.

The total beam lens 45 is arranged such that the first spectral partial beam 32 is focused at a first focal point 46, which is arranged between the first dichroic splitter mirror 35 and the first partial beam mirror 37. A partial beam lens 48 between the partial beam mirrors 37, 38 is arranged such that the first spectral partial beam 32 is put into a collimated state upon passing through the partial beam lens 48. By means of the objective lens 19, the first partial beam 32 is focused onto the front section 40 of the eye.

The second spectral partial beam 33 is focused at a second focal point 47, which is arranged between the first dichroic splitter mirror 35 and the second dichroic splitter mirror 36. The distance between the first focal point 46 and the objective lens 49 corresponds to the focal length of the objective lens 19, such that the second spectral partial beam 33 is put into a collimated state upon passing through the objective lens 19. Upon passing through the cornea and the eye lens, the second spectral partial beam is focused onto the back section 41 of the eye.

In order to scan the object regions 40, 41 for the purpose of imaging in a lateral direction, the object beam path 23 is deflected by an angle from the optical axis of the system by the scanning mirrors 27, 28. The total beam lens 45 focuses the beam and in so doing converts the angle of the beam into a lateral offset of the focal points 46, 47 in the respective focal plane thereof. In the case of the second spectral partial beam 33, the lateral position of the second focal point 47 is converted by the objective lens 19 into a beam angle at which the second spectral partial beam 33 is directed onto the pupil of the eye. The partial beam 33 which is collimated upon impingement is focused onto the retina by the cornea and the eye lens. By changing the angle of the scanning mirrors 27, 28, the second spectral partial beam 33 scans the retina of the eye. The second spectral partial beam 33 thus enables imaging in the back section 41 of the eye.

Analogously, in the case of the first spectral partial beam 32, the first focal point 46 is scanned laterally in the focal plane thereof. The partial beam lens 48 collimates the first spectral partial beam 32, which is then focused onto the front section 40 of the eye by the objective lens 19. The partial beam lens 48 translates the lateral position of the first focal point 46 into a beam angle, which is in turn translated into a lateral position by the objective lens 19. By means of the actuation of the scanning mirrors 27, 28, the front section 40 of the eye can thus be scanned by way of the first spectral partial beam 32, thus enabling imaging of the front section 40 of the eye.

If the second dichroic splitter mirror 36, the second partial beam mirror 38 and the objective lens 19 are displaced along the beam direction of the second partial beam path 33 relative to the first spectral splitter mirror 35 and the first partial beam mirror 37 and the distance between the objective lens 19 and the eye 14 is maintained in the process, then the focus position of the second spectral partial beam 33 in relation to the back section 41 of the eye changes, while the focus position of the first spectral partial beam 32 in relation to the front section 40 of the eye remains unchanged. It thus becomes possible to focus the second spectral partial beam 33 onto the back section 41 of the eye even in the case of patients having defective vision.

In the exemplary embodiments described hitherto, the wavelength-dependent beam splitters are configured as dichroic splitter mirrors 35, 36, such that one portion of the frequencies of the OCT light 15 is reflected and another portion of the frequencies of the OCT light 15 is transmitted. The invention can also be realized with other types of wavelength-dependent beam splitters.

Figure 8:
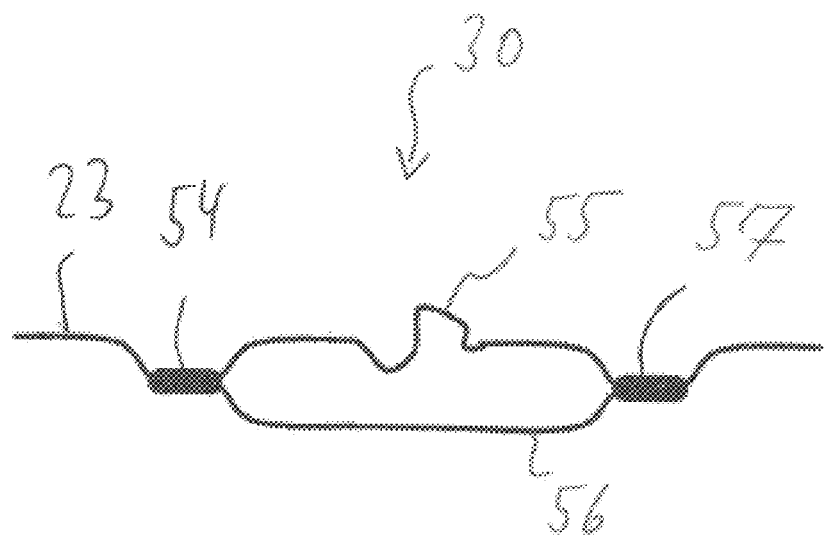

FIG. 8 illustrates an exemplary embodiment in which the parallel section 30 of the object beam path 23 is realized by means of optical waveguides of different lengths. The OCT light of the object beam path impinges on a fiber coupler 54, which guides the OCT light either into a first fiber 55 or into a second fiber 56 in a frequency-dependent manner. After path distances of different lengths have been covered, the first spectral partial image 32 and the second spectral partial image 33 are recombined in a second fiber coupler 57. The first fiber coupler 54 corresponds in terms of its function to the first spectral splitter mirror 35; the second fiber coupler 57 corresponds in terms of its function to the second spectral splitter mirror 36. Exactly as in all the variants described above, the parallel section 30 can be arranged either in the object beam path 23 or in the reference beam path 24.

Figure 9:
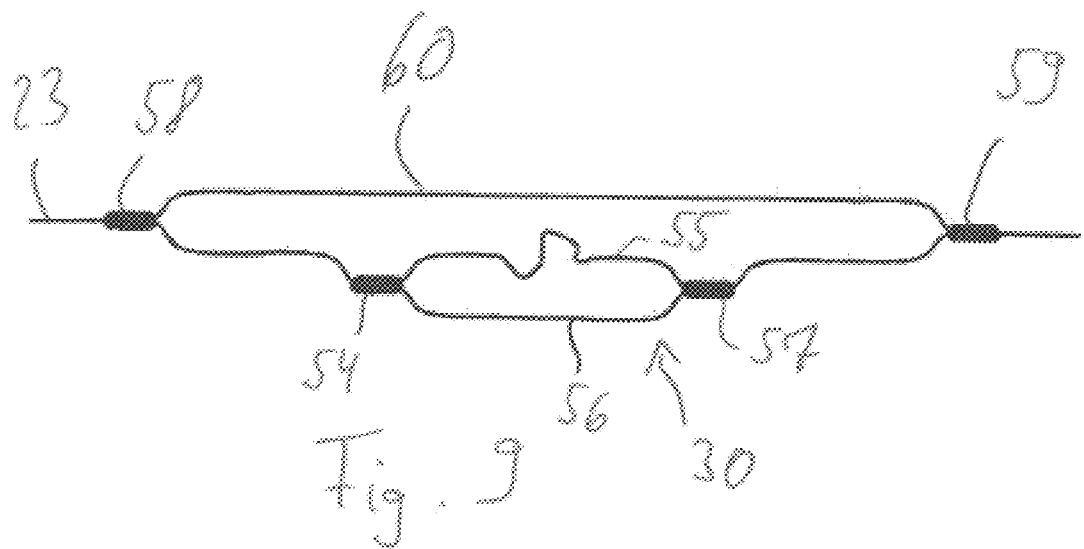

In the case of the further variant in accordance with FIG. 9, a third fiber 60 is provided, which can guide the object beam path 23 past the parallel section 30. If the entire spectrum of the OCT light is guided onto an object region, this results in a measurement with improved axial resolution. The switchover between the parallel section 30 and the third fiber 60 is effected by way of fiber-optic switching elements 54, 57, which, in a similar manner to a switch, connect a path on one side to one of two paths on the other side in a light-guiding manner. The switchover between the two paths is effected by means of a digital electrical signal. The switchover to the third fiber 60 corresponds to the unit 42 that comprises the dichroic splitter mirrors 35, 36 being swung out of the beam path in the exemplary embodiments described above.

The invention claimed is:

1. An OCT system comprising an OCT light source for emitting OCT light into an object beam path and a reference beam path and comprising a detector for picking up an interference signal generated from the object beam path and the reference beam path, wherein a wavelength-dependent beam splitter is arranged in an OCT beam path comprising the object beam path and the reference beam path, such that a first spectral partial beam is guided along a longer path distance and that a second spectral partial beam is guided along a shorter path distance, wherein both the first spectral partial beam and the second partial spectral beam are illuminated on a sample, wherein the OCT light source is a single unified OCT light source which generates narrowband light tuned over a continuous frequency range that includes the OCT light for the first spectral partial beam and for the second spectral partial beam, and wherein the OCT light source generates the first spectral partial beam and the second spectral partial beam by means of a unified tuning process wherein the first spectral partial beam and the second spectral partial beam are within said continuous frequency range.

2. The OCT system of claim 1, wherein the OCT beam path comprises a parallel section, in which the first spectral partial beam is guided along a first parallel path and in which the second spectral partial beam is guided along a second parallel path.

3. The OCT system of claim 2, wherein a first wavelength-dependent beam splitter is arranged at an input of the parallel section and a second wavelength-dependent beam splitter is arranged at an output of the parallel section.

4. The OCT system of claim 2, wherein a path length difference between the first parallel path and the second parallel path is adjustable.

5. The OCT system of claim 4, wherein a distance between a partial beam mirror arranged in the parallel section and the wavelength-dependent beam splitter is adjustable.

6. The OCT system of claim 2, comprising a partial beam lens arranged in the parallel section.

7. The OCT system of claim 6, wherein the partial beam lens is adjustable such that the focus position of the relevant spectral partial beam can be displaced in an axial direction.

8. The OCT system of claim 2, comprising a total beam lens arranged outside the parallel section, which total beam lens focuses the first spectral partial beam at a first focal point within the parallel section and focuses the second spectral partial beam at a second focal point within the parallel section.

9. The OCT system of claim 8, wherein the total beam lens is arranged between a scanning device and the parallel section.

10. The OCT system of claim 1, wherein in a first state a wavelength-dependent beam splitter is arranged in the OCT beam path and in a second state the wavelength-dependent beam splitter is not arranged in the OCT beam path.

11. The OCT system of claim 10, comprising an actuator, which is used to adjust the distance between the partial beam mirror and the wavelength-dependent beam splitter and which is used to change between the first state and the second state of the wavelength-dependent beam splitter.

12. The OCT system of claim 1, wherein an axial focus position of the first spectral partial beam deviates from an axial focus position of the second spectral partial beam.

13. The OCT system of claim 1, wherein the first spectral partial beam impinges on a measurement object at a different angle than the second spectral partial beam.

14. An OCT method in which OCT light is emitted and is split into an object beam path and a reference beam path, wherein an interference signal generated from the object beam path and the reference beam path is picked up by a detector and wherein a wavelength-dependent beam splitter is arranged in the beam path of the OCT light, such that a first spectral partial beam of the OCT light is guided along a longer path distance and that a second spectral partial beam of the OCT light is guided along a shorter path distance, wherein both the first spectral partial beam and the second partial spectral beam are illuminated on a sample, wherein the OCT light for the first spectral partial beam and for the second spectral partial beam is provided by a single unified OCT light source which generates narrowband light tuned over a continuous frequency range that includes the OCT light for the first spectral partial beam and for the second spectral partial beam, and wherein the unified OCT light source generates the first spectral partial beam and the second spectral partial beam by means of a unified tuning process wherein the first spectral partial beam and the second spectral partial beam are within said continuous frequency range.

* * * * *